United States Patent
Rasmussen et al.

(10) Patent No.: US 8,921,518 B2
(45) Date of Patent: Dec. 30, 2014

(54) PURIFICATION OF PROTEINS USING PREPARATIVE REVERSE PHASE CHROMATOGRAPHY (RPC)

(75) Inventors: Daniel E. Rasmussen, Copenhagen O (DK); Arne Staby, Bagsvaerd (DK); John Strikart Nielsen, Kastrup (DK); Ole Schou, Stensved (DK)

(73) Assignee: Novo Nordisk A/S, Bagsvaerd (DK)

( * ) Notice: Subject to any disclaimer, the term of this patent is extended or adjusted under 35 U.S.C. 154(b) by 383 days.

(21) Appl. No.: 12/158,759

(22) PCT Filed: Dec. 21, 2006

(86) PCT No.: PCT/EP2006/070103
§ 371 (c)(1),
(2), (4) Date: Sep. 11, 2008

(87) PCT Pub. No.: WO2007/071768
PCT Pub. Date: Jun. 28, 2007

(65) Prior Publication Data
US 2009/0036652 A1    Feb. 5, 2009

Related U.S. Application Data

(60) Provisional application No. 60/753,653, filed on Dec. 23, 2005.

(30) Foreign Application Priority Data

Dec. 23, 2005   (EP) ..................................... 05112865

(51) Int. Cl.
| | | |
|---|---|---|
| C07K 1/16 | (2006.01) | |
| C07K 14/52 | (2006.01) | |
| C07K 1/20 | (2006.01) | |
| C07K 14/53 | (2006.01) | |
| C07K 14/54 | (2006.01) | |
| C07K 14/435 | (2006.01) | |

(52) U.S. Cl.
CPC . *C07K 14/52* (2013.01); *C07K 1/20* (2013.01); *C07K 14/53* (2013.01); *C07K 14/54* (2013.01)
USPC ............ 530/351; 530/415; 530/416; 530/417

(58) Field of Classification Search
None
See application file for complete search history.

(56) References Cited

U.S. PATENT DOCUMENTS

| | | | |
|---|---|---|---|
| 5,446,024 A * | 8/1995 | Builder et al. .................. | 514/12 |
| 6,756,484 B1 | 6/2004 | Brierley et al. | |
| 2003/0003545 A1 | 1/2003 | Ebner et al. | |
| 2005/0124044 A1 | 6/2005 | Cunningham et al. | |

FOREIGN PATENT DOCUMENTS

| | | |
|---|---|---|
| EP | 531639 | 3/1993 |
| GB | 2037296 | 7/1980 |
| JP | 6-225767 | 8/1994 |
| JP | 2001-521044 A | 11/2001 |
| JP | 2002-511484 A | 4/2002 |
| JP | 2005-535286 A | 11/2005 |
| WO | WO 86/07594 | 12/1986 |
| WO | 99/21889 A1 | 5/1999 |
| WO | 99/53056 A1 | 10/1999 |
| WO | 03/066676 A1 | 8/2003 |
| WO | WO 2004/055168 | 7/2004 |
| WO | 2005/019262 A1 | 3/2005 |
| WO | WO 2005/035565 | 4/2005 |

OTHER PUBLICATIONS

Wang et al, Cancer Research, 2003. vol. 63, pp. 9016-9022.*
Carr, David.The handbook of analysis and purification of peptides and proteins by reversed-phase HPLC, published by Grace Vydac, 2002, 36 pages.*
Hancock, WS et al., Science, 1978, vol. 200, pp. 1168-1170.
Friesen, Heinz-Jurgen, Practical Apsects of Modern HPLC, 1982, pp. 77-107.
McNay, Jennifer L. M. et al., Biotechnology and Bioengineering, 2001, vol. 76, No. 3, pp. 233-240.
Hearn, M. T. W., Book: Biochromatography, Theory and Practice, Ed: M.A. Vijayalakshmi, 2002, Chapter 5, pp. 72-141.
Wang et al., Biochemical Journal, 2001, vol. 354, pp. 161-168.
Chlenov et al., Journal of Chromatography, 1993, vol. 631, pp. 261-267.
Teshima et al., Journal of Chromatography, 1992, vol. 625, pp. 207-215.
Chenlov et al., "High-Performance Liquid Chromatography of Human Glycoprotein Hormones," Journal of Chromatography, 1993, vol. 631, pp. 261-267.
Amersham Biosciences, "Reversed Phase Chromatography. Principles and Methods Passage" 1999, pp. 1-86, XP007910872.

* cited by examiner

*Primary Examiner* — Bridget E Bunner
*Assistant Examiner* — Fozia Hamud
(74) *Attorney, Agent, or Firm* — Nonna G. Akopyan; Reza Green; Richard W. Bork

(57) ABSTRACT

The present invention provides a method for industrial-scale protein separation by reverse phase chromatography by use of a buffer system and an additional salt.

9 Claims, 6 Drawing Sheets

PURIFICATION OF PROTEINS USING PREPARATIVE REVERSE PHASE CHROMATOGRAPHY (RPC)

CROSS-REFERENCE TO RELATED APPLICATIONS

This application is a 35 U.S.C. §371 national stage application of International Patent Application PCT/EP2006/070103 (published as WO 2007/071768), filed Dec. 21, 2006, which claimed priority of European Patent Application 05112865.0, filed Dec. 23, 2005; this application further claims priority under 35 U.S.C. §119 of U.S. Provisional Application 60/753,653, filed Dec. 23, 2005.

FIELD OF THE INVENTION

The present relation relates to novel chromatographic methods suitable for protein purification.

BACKGROUND OF THE INVENTION

In the pharmaceutical industry, purification is an integrated part of producing molecules for medical needs. Both biopharmaceutical molecules derived from recombinant techniques and more traditional smaller molecules derived from organic synthesis are generated, and in both cases chromatographic purification techniques play an essential role in production methods. Chromatographic techniques include separation based on ion-exchange, hydrophobic interaction etc. In reversed phase chromatography (RPC) a molecule in solution binds to the hydrophobic surface or hydrophobic ligand of a chromatographic resin. The partitioning of the molecule between the solution and the resin occurs as a result of hydrophobic interactions between the molecule with hydrophobic patches at its surface and the hydrophobic surface on the resin. A solvent of increasing hydrophobicity is subsequently used to dissociate or elute the bound molecule at a point at which the hydrophobic interaction between the exposed patches and the resin is less favourable than the interaction between the bound molecule and the solvent. The molecule then releases from the resin and elutes. Separation of different molecules in the same solution occurs if the molecules have different hydrophobicity and therefore elute at different point in time when the hydrophobicity of the eluting solvent is increased.

In general, RPC is capable of distinguishing between molecules with very small differences in hydrophobicity and it is thus regarded as a very powerful separation tool and the preferred method in analytical chromatography. RPC is applied for preparative use as well; however, RPC is usually used for purification of smaller molecules and peptides that can withstand the harsh operating conditions including organic solvents. Larger molecules, such as proteins denature more easily and preparative RPC is therefore generally considered to be unsuitable for native proteins ["Reversed Phase Chromatography. Principles and Methods", Amersham Pharmacia Biotech; and "Conformation of polypeptides and protein in reversed phase and lipophilic environments" MTW Hearn in "Biochromatography, Theory and Practice" edited by M. A. Vijayalakshmi. Taylor & Francis, 2002.

Disclosures of the application of preparative RPC on larger proteins do exist. In general these applications are, however, performed in fairly small scale, and with a relatively low protein load, on a RPC column with a small diameter and with a column material with relatively small particles size (to be regarded as semi-preparative, non-industrial scale/load). Solvent system used for purification is typically acetonitrile with TFA at very low pH, and no additional salt component is applied for elution.

Wang, Y M et al., Biochem., 354, 161-168, 2001 discloses the use of RPC to purify proteases from snake venom. The protease has a molecular weight around 40 kDa, and the elution solvent was acetonitrile with 0.07% (v/v) trifluoro acetic acid (TFA). The purification was performed on a VYDAC $C_4$ column (4.6×250 mm).

Chlenov, M A et al. J Chromatogr. 1993, 631(1-2), 261-267, discloses the use of RPC at neutral pH to purify biological active thyroid stimulating hormone, luteinizing hormone and chorionic gonaditropin, all with a molecular weight>30 kDa. All three purifications were performed in a 0.1 M sodium phosphate containing solvent, pH 6.8, on a VYDAC 214TP, $C_4$ column (4.6×250 mm). Acetonitrile was used as eluting solvent. Load volume was 20 µl.

Teshima G and Canova-Davis E, J Chromatogr. 1992, 625 (2), 207-215, describes the purification of $H_2O_2$-treated human growth hormone on a Polymer Labs PLRP-S RPC-column (300 Å, 10 µm, 7.5×300 mm). The purification was performed in 25 mM ammonium acetate, pH 7.5. The protein was eluted with a 34% to 39% 1-propanol gradient. The purification was performed at 40° C. and at a flow rate of 1 ml/min.

Because of the resolving power of RPC and the need to purify native proteins with high purity, e.g. for therapeutic use, it is desirable to have methods which provide improved or alternative ways of applying RPC in the field of protein separation in industrial scale, including using industrially suitable column loads and retaining substantial levels of bioactivity of the purified protein.

SUMMARY OF THE INVENTION

The present inventors have surprisingly found that the addition of salt and a buffer to the eluting solvent increases the separating power of RPC. Accordingly, the present invention relates to a method for purifying a protein from a composition, the method comprising loading a solution of said composition onto a reversed phase liquid chromatography column and eluting said protein from the column with a solvent containing a buffer and a salt, wherein said salt does not have buffering capacity at the pH of the buffer used.

DESCRIPTION OF THE INVENTION

Figure 1:
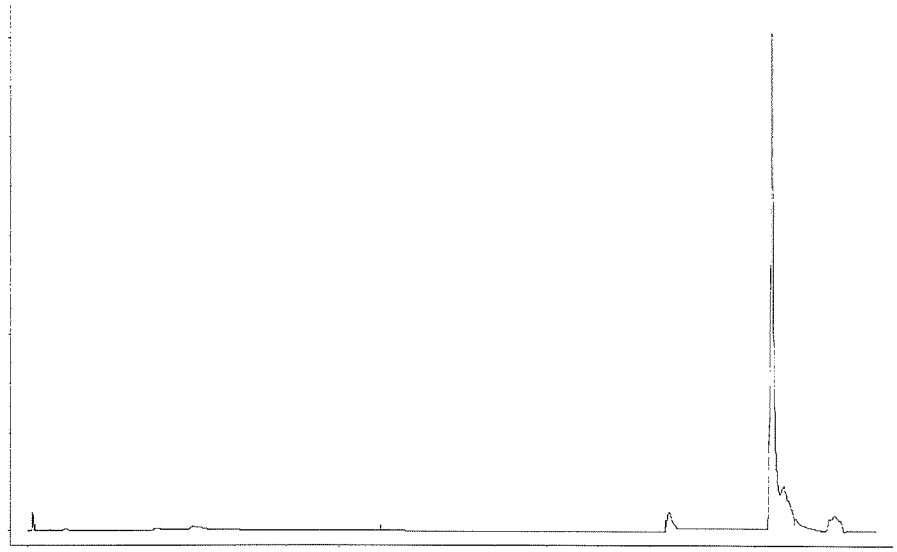
FIG. 1 is a chromatogram of IL-21 purification on a CN-propyl substituted silica gel where no salt is added to the chromatographic solvents, cf. example 1.

The present invention provides a method for industrial-scale protein separation by reverse phase chromatography. In one aspect the method applies column loads in the range of 0.1-200 mg/mL of column material. The method further provides a gentle way of purifying proteins in industrial-scale, i.e. a method wherein a substantial amount of the loaded protein survives the operating conditions and retains its bioactivity.

The present invention provides a method for purifying proteins by means of RPC, wherein said method increases the separating power of RPC. To increase separating power means to provide a better resolution, $R_s$, i.e. to increase the difference in retention time (increased selectivity) or volume between two proteins to be separated or to reduce peak width of the eluted protein (increased efficiency)

$$R_s = 2\frac{V_{R,B} - V_{R,A}}{W_B + W_A} \quad (1)$$

wherein $V_{R,B}$ and $V_{R,A}$ are the retention volume of components B and A, respectively, and $W_B$ and $W_A$ are the peak width of components B and A, respectively. Retention volume is the volume of solvent at which a solute leaves the column. In the methods of the present invention, proteins are eluted in sharper peaks, which intrinsically lead to better separation or even base line separation. The increase in separation makes it possible to increase the load of a RPC chromatographic column and thereby reduce size of the RPC column without compromising purity of the eluate pool. The increased load reduces the need for RPC chromatographic media and thus improve overall process economy when utilizing RPC in industrial scale, where large volumes of expensive RPC chromatographic media are used.

The term "industrial scale" is meant to include processes, wherein the RPC columns used are at least 0.1 l, such as at least 0.2 l, at least 0.5 l, at least 1 l, at least 2 l, at least 5 l, at least 20 l, at least 50 l, or such as at least 100 l. "Industrial scale" is also meant to include processes wherein the amount of polypeptide applied to the column is at least 0.01 g, such as at least 0.02 g, at least 0.05 g, at least 0.1 g, at least 0.2 g, at least 0.5 g, at least 1 g, at least 2 g, at least 5 g, at least 10 g, at least 20 g, at least 50 g, at least 100 g, at least 100 g, at least 200 g, at least 500 g, at least 1000 g, at least 2000 g, at least 5000 g, or such as at least 10000 g.

An improved separation may be realised simply by visual inspection of the chromatogram, e.g. by noting increases in the difference in retention times or volumes, base line separation, or the appearance of sharper and more well-defined peaks. The increase in separation power may also be quantified as the number of theoretical plates, N, where N may be calculated as follows $$N = 5.54\left(\frac{V_R}{W_{1/2}}\right)^2 \quad (2)$$

wherein $V_R$ is the retention volume and $W\frac{1}{2}$ is the peak width at half peak height. The above equation describes N when eluting in isocratic mode. The number of N has also been described for gradient elution (in ion exchange chromatography) by S Yamamoto et al. in "Ion-exchange Chromatography of Proteins. Chapter two: Theoretical Aspects", Marcel Dekker, 1988. To be able to compare columns of different length the Height Equivalent to a Theoretical Plate (HETP) may be calculated as $$HETP = \frac{L}{N} \quad (3)$$

wherein L is the length of the column. The lower HETP the better the separation. An improved separation may provide for the separation of otherwise un-separable proteins, it may provide for an improved yield in a separation step, or it may provide for an improved loading on to the column thus improving process economy. If two peaks are closely spaced, it may be necessary to collect only a fraction of the peak of interest to obtain the desired purity. If peak separation is improved, a larger fraction of the peak may thus be collected.

The present invention concerns a method for purifying a protein from a composition comprising said protein and at least one undesired impurity, the method comprising loading a solution of said composition onto a reversed phase liquid chromatography column and eluting said protein from the column with a solvent containing a buffer and a salt, wherein said salt does not have buffering capacity at the pH of the buffer used.

In the present context a protein is intended to indicate a polypeptide, i.e. amino acids interconnected via peptide bonds. It is to be understood that proteins may contain additional groups, such as prosthetic groups, e.g. heme groups, and/or conjugated groups, such as polyalkylene oxide (PAO), including polyalkylene glycol (PAG) (e.g. polyethylene glycol (PEG), polypropylene glycol (PPG), branched PEGs), dendrimers, polyvinyl alcohol (PVA), polycarboxylate, polyvinylpyrolidone, polyethylene-co-maleic acid anhydride, polystyrene-co-maleic acid anhydride, and dextran, including carboxymethyl-dextran, fatty acids, cyclodextrins, dextrans, albumins, or an antibody or part of an antibody optionally containing a Fc-domain. As used herein, the term "dendrimer" means a structurally well-defined branched polymers made from a precise number of monomer units, as described, e.g., in WO 2005/014049, WO 2002/020033, Grayson and Frechet (Chem. Rev. 2001, 101, 3819), Gillies and Frechet (J. Amer. Chem. Soc. 2002, 124, 14137-14146). The molecular weight of dendrimers is typically in the range of 700-10.000 Da. The present invention is advantageous for use when purifying proteins having a biological activity, as the method is developed to retain as much biological activity as possible, but the method may also be used on proteins, which do not have a biological function, if it is desired to purify such proteins.

The term "purifying" a protein from a composition comprising the protein and one or more contaminants means increasing the degree of purity of the protein in the composition by reducing the contents of at least one contaminant from the composition. The contaminants may be related impurities or non-related impurities. Non-related impurities may include, without limitation, host cell proteins (HCP), DNA, coloured impurities, lipids, salts, buffers, reagents from a chemical or enzymatic modification of the protein e.g. heme groups, polyalkylene oxide (PAO), including polyalkylene glycol (PAG) (e.g. polyethylene glycol (PEG), polypropylene glycol (PPG), branched PEGs), polyvinyl alcohol (PVA), polycarboxylate, poly-vinylpyrolidone, polyethylene-co-maleic acid anhydride, polystyrene-co-maleic acid anhydride, and dextran, including carboxymethyl-dextran, fatty acids, cyclodextrins, dextrans, albumin, or an antibody or part of an antibody optionally containing a Fc-domain. The term "related impurity" as used herein means an impurity that has a structural resemblance to the target protein but has different chemical or physical structure compared to the target protein. Related impurities may include, without limitation, truncated forms, extended forms (extra amino acids, various derivatives, etc.), deamidated forms, incorrectly folded forms, forms with undesired glycosylation including sialylation, oxidated forms, forms resulting from racemization, forms lacking amino acids in the intra-polypeptide chain, forms having extra amino acids in the intra-polypeptide chain, forms having replacements of amino acids in the intra-polypeptide chain, forms wherein a chemical or enzymatic modification has taken place on another residue than desired.

The term "derivative" as used herein in relation to a parent protein means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like.

The term "truncated forms" as used herein in relation to a protein means any fragment of the protein having at least 20% of the amino acids of the parent protein, such as 35%, 50%, or 75%. Thus, for human serum albumin a fragment would comprise at least 117 amino acids as human serum albumin has 585 amino acids.

The solvent used to elute the protein comprises a buffer. A buffer is a mixture of an acid (HA) and its conjugated base ($A^-$). A buffer is capable of resisting changes in pH as the result of addition of acid or base. This resistance (buffer capacity) is largest when pH is close to the pKa of the acid HA. In practical life, a mixture of an acid and the conjugated base is regarded as a buffer if the pH of the solution is within two pH units, such as within one pH unit from the pKa value of the acid. Examples of buffers which can be applied in the present invention include acetate buffers, phosphate buffers, citric acid buffers, lactic acid buffers, TRIS buffers, CHAPS buffers, borate buffers, HEPES buffers, carbonate buffers, histidine buffers, MES buffers, ascorbic buffers, and mixtures of two or more of these. It is standard in the art to add trifluoro acetic acid (TFA) to RPC solvents to adjust pH. The omission of TFA in the solvents used in the methods of the present invention is regarded as an advantage due to the well-established environmental and occupational health problems connected to the use of TFA.

Typical buffer concentrations to be used in the present invention are between 0.02 and 20 (w/w) %, such as between 0.05 and 5 (w/w) %, such as between 0.1 and 0.2 (w/w) %.

Typically pH of solvents to be used in the present invention is within the range of 1-13, such as 2-13, such as 3-13, such as 3.5-13, such as 4-13, such as 4.5-13, such as 5-13, such as 5.5-13, such as 6-13, such as 6.5-13, such as 7-13, such as 7.5-13, such as 8-13, such as 1-12, such as 1-11, such as 1-10, such as 1-9.5, such as 1-9, such as 1-8.5, such as 2-10, such as 3-9.5, such as 3.5-9.5, such as 4-9.5, such as 4.5-9.5, such as 5-9.5, such as 5.5-9.5, such as 6-9.5, such as 6.5-9.5, such as 7-9.5, such as 7.5-9.5, such as 8-9.5, such as 3-9, such as 3.5-9, such as 4-9, such as 4.5-9, such as 5-9, such as 5.5-9, such as 6-9, such as 6.5-9, such as 7-9, such as 7.5-9, such as 8-9, such as 3-8.5, such as 3.5-8.5, such as 4-8.5, such as 4.5-8.5, such as 5-8.5, such as 5.5-8.5, such as 6-8.5, such as 6.5-8.5, such as 7-8.5, such as 7.5-8.5, such as 8-8.5, such as 3-8, such as 3.5-8, such as 4-8, such as 4.5-8, such as 5-8, such as 5.5-8, such as 6-8, such as 6.5-8, such as 7-8, such as 7.5-8.

Various factors may influence the choice of the pH at which to purify a given protein according to the method of the present invention, and in particular, the pI of the protein is important. When pH of a solution is the same as the pI of a dissolved protein, the solubility of the protein is lowest and the risk of precipitation is highest. Normally it is desirable to use a pH which is at least one or two pH units away from the pI of the protein to be purified, although pH close to or at the pI of the protein to be purified can be used if solubility of the protein is not a problem. This, of course, also influences the choice of buffer in that a given conjugated acid-base pair is only effective as a buffer when the pH is close to the pKa of the acid in the given solvent.

The solvent used to elute the protein comprises a salt in solution. The term salt is used for ionic compounds composed of positively charged cations (X) and negatively charged anions (Y), so that the product is neutral and without a net charge. Both X and Y may be multiply charged so that the ratio X:Y may be different from 1:1.

The salt used together with the buffer does not have any significant buffering capacity at the pH achieved with the specific buffer used and are thus not part of the buffer system itself. In one embodiment, the $pK_a$ of the salt is at least one pH unit removed from the $pK_a$ of the buffer used. In a further embodiment, the $pK_a$ of the salt is at least one pH unit removed from the pKa of the buffer used. The choice of salt to be used together with the buffering system will naturally depend on the choice of buffer, but when working at a pH range usual for handling proteins, examples of salts which can be applied in the present invention could include halides, such as chlorides, bromides, iodines; sulphates; borates; lactates; and citrates, and mixtures of two or more thereof. Examples of the positively charged counter ion include sodium; potassium; magnesium; calcium; and ammonium. Specific examples of salts include potassium chloride; sodium chloride; ammonia chloride and potassium lactate.

Typical salt concentrations to be used in the present invention are between 0.02 and 30 (w/w) %, such as between 0.05 and 10 (w/w) %, such as between 0.16 and 1.1 (w/w) %.

The method of the present invention may be run at a range of temperatures depending on e.g. the type of protein to be purified. If the temperature is too high, the protein may denature irreversible, and if the temperature is too low, mechanical problems may arise due to increased viscosity of the solvent. An adjustment of the temperature within these limits may be used to increase the separation of two proteins if the hydrophobicity of the two proteins has different temperature dependence. Generally, the methods of the present invention may be run at temperatures from 0-80° C., such as from 10-60° C., 20-60° C., 20-50° C., or 20-40° C.

In one embodiment, the solvent used in the methods of the present invention is an aqueous solvent comprising water and an organic component. Typical organic components include acetonitrile or alcohols.

In one embodiment, the organic component is an alcohol, and in one embodiment, the solvent is a mixture of water and an alcohol. Particular mentioning is made of mono-alcohols, i.e. alcohols comprising only one alcohol group. Examples of mono-alcohols which can be used in the methods of the present invention include methanol, ethanol, 1-propanol and 2-propanol, and mixtures of two or more thereof. It is regarded as an additional advantage to use alcohols rather than acetonitrile due to the well-established environmental and occupational health problems connected to the use of acetonitrile.

The proteins are eluted with an increasing hydrophobicity of the solvent, i.e. by increasing the concentration of the organic compound. The concentration of the solvent used to load the protein on to the column depends on the nature of the protein and the hydrophobicity of the organic compound. This solvent is often referred to as the equilibration solvent as the column has typically been washed or equilibrated with one or more column volumes of this solvent prior to the loading of the protein to the column. A typical concentration of the organic compound in the equilibrating solvents is from 0-80%, such as 10-70%, 10-60%, or 20-50%. The concentration is upward limited by the denaturing effect of the organic component. If the concentration is too high, there is a risk that the protein may irreversible denature. During elution of the protein, the concentration of the organic component in the solvent is raised, typically to concentrations from 5-96%, such as 10-95%, 20-90%, 30-90%, or 40-80%.

Elution derived from the increase in the concentration of the organic component in the solvent (often referred to as the gradient) may be brought about in a number of ways. The gradient may be linear, stepped comprising one or more steps, isocratic or curved. Elution may also be performed in isocratic mode, that is, by constant organic component concentration. The elution scheme may also be applied in any combination of the above gradients and isocratic elution mode, e.g. an elution scheme may be a linear gradient followed by an isocratic elution followed by a step and followed by a linear gradient again, or it may be a linear gradient followed by another linear gradient.

Reversed phase column material is made of a resin to which as hydrophobic material may be attached. Typical resin materials are silica and polystyrene; hydrophobic ligands may optionally be attached. In case of substituted resins, the resin is substituted with a hydrophobic ligand, typically selected from (but not limited to) aliphates, such as $C_2$, $C_4$, $C_6$, $C_8$, $C_{10}$, $C_{12}$, $C_{14}$, $C_{16}$, or $C_{18}$ or derivates of these, e.g. cyanopropyl (CN-propyl), or branched aliphates, or benzene-based aromates, such as phenyl, or other polar or non-polar ligands. The ligand may be a mixture of two or more of these ligands. Suitable polystyrene based resins include, without limitation, resins supplied by Rohm Haas (e.g. Amberlite XAD or Amberchrom CG), PolymerLabs (e.g. PLRP-S), GE Healthcare (e.g. Source RPC), Applied Biosystems (e.g. Poros R).

The manufacturing processes for and optimal features of the column material often require that a linking group also called a spacer is inserted between the resin and the ligand.

Other parameters in the methods of the present invention include load, i.e. amount of protein which is loaded to the column and flow rate. These parameters may be optimised through experiments which are known to the person skilled in the art. The protein is typically loaded onto the column in a concentration of at least about 0.1 mg per mL of resin, such as, e.g., at least about 0.2 mg, 0.5 mg, 1 mg, 2 mg, 5 mg, 10, or 20 mg per mL of resin; or in the range of 0.1-200 mg, such as, e.g., 0.1-100 mg, 0.5-100 mg, 1-50 mg, or 2-30 mg per mL of resin; preferably the load is at least 1 mg per mL resin. Measurement of packed resin volume is typically done in suspension or similar mode.

The protein is typically applied at a flow of 1-200 column volumes per hour (CV/h), such as at least 1 CV/h, such as at least 2 CV/h, such as at least 3 CV/h, such as at least 4 CV/h, such as at least 5 CV/h, such as at least 6 CV/h, such as at least 8 CV/h, such as at least 10 CV/h, such as at least 12 CV/h, e.g. at least 20 CV/h or at least 40 CV/h or at least 80 CV/h, e.g. 80-120 CV/h.

When the protein is eluted from the column it is dissolved in a solvent with a relatively high concentration of the organic component, which may harm the protein over time due to its denaturing effects. In one embodiment of the invention, the protein is therefore transferred to another solvent/medium immediately after elution, e.g. by dilution, ultrafiltration, precipitation, crystallisation, desalting, gel filtration or by binding the protein onto another chromatographic medium (ion exchange-, hydrophobic interaction-, affinity or metal chelate medium) and washing out the denaturing solvent and eluting the protein.

In one embodiment, the protein to be purified according to the method of the present invention have a molecular weight between 10 and 200 kDa, such as between 12 and 150 kDa, or between 12 and 120 kDa, or between 12 and 100 kDa or between 12 and 50 kDa or between 12 and 40 or between 15 and 40. Particular mentioning is made of cytokines such as Interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, ciliary neutrophic factor, cardiotrophin-1, cardiotrophin-1 like cytokine, leukemia inhibitory factor, oncostatin M, granulocyte colony stimulating factor, granulocyte macrophage stimulating factor, granulocyte stimulating factor, erythropoietin, growth hormone, prolactin, interferon α, interferon γ, stem cell factor, placental lactogen, ciliary neutrophic factor, tumor necrosis factor, B-cell activating factor (BAFF), and macrophage chemotactic factor.

In one embodiment, the protein to be purified retains at least 50% of its bioactivity during the RPC purification step, preferably at least 60%, 75%, or 90%. The bioactivity can be measured by any means available in the art and the choice of assay will naturally depend on the biological activity of the protein.

In one embodiment, the method of the present invention comprises the steps of
  a) Loading IL-21 onto a RPC column, equilibrated with a solvent comprising water, 25-35 (w/w) % ethanol, 0.1-0.3 (w/w) % Tris, 0.5-1.0 (w/w) % KCl, pH 6-8, up to 20 g/l column material,
  b) Washing the column with up to 5 column volumes of the equilibration solvent,
  c) Eluting IL-21 in a linear gradient from 0 to 100% of an elution solvent comprising 50-70% (w/w) % ethanol, 0.1-0.3 (w/w) % Tris, 0.5-1.0 (w/w) % KCl, pH 6-8,
  d) Collecting the IL-21-containing fractions,
  e) Washing the column with up to 10 column volumes of the elution solvent,
  f) Regenerating the column with a 50-70% 1-propanol containing solvent.

Industrial-Scale Production and Purification

The present invention is particular useful for industrial-scale production and purification of proteins. In such processes, a protein is typically produced by means of a cell culture or fermentation.

Thus, the present invention also provides an industrial-scale process for the production and purification of a desired protein, said process including the steps of:
  (i) producing a crude bulk of a desired protein in a cell culture or fermentation; and
  (ii) purifying said crude bulk by a purification sequence utilizing one or more reverse phase chromatography (RPC) processes;

wherein at least one of such reverse phase chromatography processes is conducted as defined hereinabove.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

General Methods

Preparation of Chromatographic Solvents

The desired amount of buffer (w/w) % and salt (w/w) % is weighted out. Water is added to dissolve the buffer and salt. The desired amount of alcohol (w/w) % (100% ethanol, 100% 1-propanol, 100% 2-propanol) is added. Water is added to 95-98% of total weight of solvent. pH is adjusted in the solvent at room temperature when solvents are used at room temperature and 30° C. Solvents used at 40° C. and 50° C. are pH-adjusted at 40° C. and 50° C. respectively. Prior to use the pH-meter is calibrated with IUPAC standard solutions at room temperature (20-25° C.). Water is added to 100%.

Determination of IL-21 Concentration

The content of IL-21 is determined by RP-HPLC as described in the following: Reverse phase HPLC was run on a Jupiter C5 (Phenomenex, 4.6×50 mm, particle size of 5 µm, pore size 300 Å). Column temperature: 40° C. A-solvent: 0.1 (v/v) % TFA in Milli-Q. B-solvent: 0.1 (v/v) % TFA in acetonitrile. Gradient programme: 0-3.5 min.: 95% A+5% B; 3.5-4.0 min.: 59% A+41% B, 4.0-14.0 min.: 52% A+48% B; 14.0-14.5 min.: 5% A+95% B; 14.5-17.0 min.: 5% A+95% B. Flow rate: 1.0 mL/min. Detection wave length: 280 nm. Load: approximately 20 µg IL-21. IL-21 concentration is determined by comparing the area of the IL-21 main peak to the area of a reference standard.

Determination of IL-21 Yield

Yield (in %) was determined as the content of IL-21 in the RPC-main peak relative to the amount of IL-21 loaded onto the preparative RPC-column. Content (in mAU×ml, where AU is measured at 280 nm) in the main peak was determined by peak integration of the preparative RPC-chromatogram. Content of IL-21 (in mAU×ml) in the application sample was determined by multiplying absorbance at 280 nm of the application sample (430 mAU) with application volume (ml).

EXAMPLES

Example 1

Performing RPC-Chromatography on a CN-propyl Substituted Silica Gel without Salt in the Solvents A solution containing 10.6 mg of rhIL-21 was loaded onto a column (5×108 mm) containing a CN-propyl substituted silica gel (15 µm particle diameter, 300 Å pore size). Prior to load the column was equilibrated with 4 CV (column volume) 20 (w/w) % ethanol, 0.21 (w/w) % Tris, pH 7.0. Unbound protein was washed out with 3 CV 20 (w/w) % ethanol, 0.21 (w/w) % Tris, pH 7.0. rhIL-21 was eluted with a linear gradient over 12 CV from 20-96 (w/w) % ethanol contained in 0.21 (w/w) % Tris, pH 7.0. The column was washed with 8 CV 96 (w/w) % ethanol, 0.21 (w/w) % Tris, pH 7.0 and 5 CV water for injection (WFI).

The column was regenerated with 5 CV 60 (w/w) % 1-propanol 0.21 (w/w) % Tris, 0.52 (w/w) % KCl, pH 7.0.

The purification was performed at a flow rate of 30 column volumes pr. hour (CV/h) and at room temperature.

Chromatogram is shown in FIG. 1. From the chromatogram it is seen that IL-21 remained bound to the resin during elution with the ethanol gradient. The protein eluted in the 1-propanol containing regenerating solvent.

Example 2

Performing RPC-Chromatography on a CN-propyl Substituted Silica Gel with 0.19 (w/w) %, 0.37 (w/w) % or 0.52 (w/w) % KCl Respectively Added as Salt to the Chromatographic Solvents Three chromatographic runs were performed as described below. Only difference between the three runs was the amount of KCl added to the solvents, se table 1:

A solution containing 10.6 mg of rhIL-21 was loaded onto a column (5×108 mm) containing a CN-propyl substituted silica gel (15 µm particle diameter, 300 Å pore size). Prior to load the column was equilibrated with 4 CV (column volume) 20 (w/w) % ethanol, 0.21 (w/w) % Tris, X (w/w) % KCl (for X see table 1), pH 7.0. Unbound protein was washed out with 3 CV 20 (w/w) % ethanol, 0.21 (w/w) % Tris, X (w/w) % KCl (for X see table 1), pH 7.0. rhIL-21 was eluted with a linear gradient over 12 CV from 20-80 (w/w) % ethanol contained in 0.21 (w/w) % Tris, X (w/w) % KCl (for X see table 1), pH 7.0. The column was washed with 8 CV 80 (w/w) % ethanol, 0.21 (w/w) % Tris, X (w/w) % KCl (for X see table 1), pH 7.0 and 5 CV WFI.

The column was regenerated with 5 CV 60 (w/w) % 1-propanol 0.21 (w/w) % Tris, 0.52 (w/w) % KCl, pH 7.0.

The purification was performed at a flow rate of 30 CV/h and at room temperature.

TABLE 1

| Run | Amount KCl in solvents (X) | Yield | Efficiency, N |
| --- | --- | --- | --- |
| 1 | 0.19 (w/w) % | 72.6% | 289 |
| 2 | 0.37 (w/w) % | 75.2% | 524 |
| 3 | 0.52 (w/w) % | 78.3% | 666 |

Figure 2:
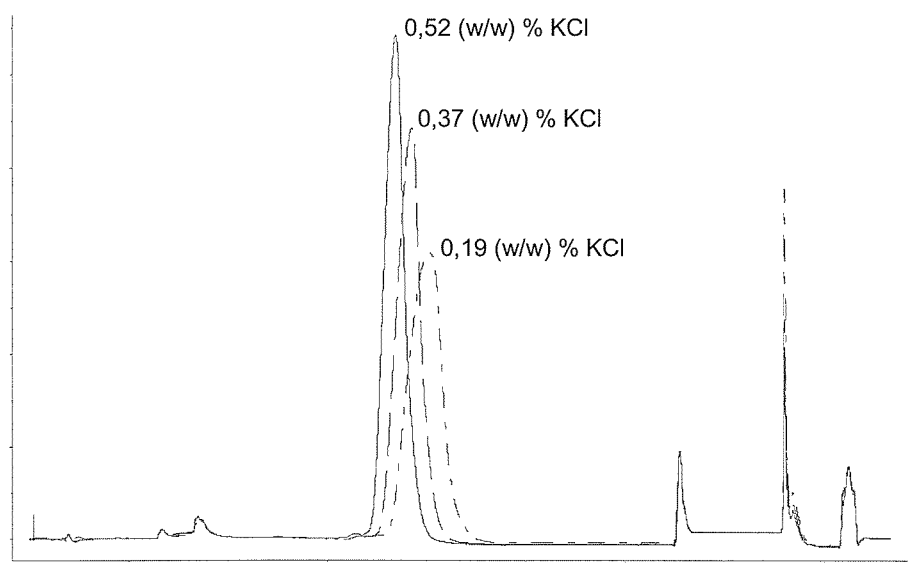
FIG. 2 is an overlay chromatogram from three purifications of IL-21 purified on a CN-propyl substituted silica gel with 0.19 (w/w) %, 0.37 (w/w) % or 0.52 (w/w) % KCl respectively added as salt to the chromatographic solvents, cf. example 2.

The three chromatograms are shown in FIG. 2. Integration of the main peaks shows that IL-21 yield increases slightly when increasing the amount of KCl in the solvents, see Table 1. Besides increasing yield the retention volume of the IL-21 peak decreases and the peak becomes narrower showing increased efficiency, N (determined by equation 2), when the KCl concentration is raised, see Table 1.

Example 3

Performing RPC-Chromatography on a di-methyl butyl Substituted Silica Gel with 0 (w/w) % or 0.52 (w/w) % Respectively Added as Salt to the Chromatographic Solvents Two chromatographic runs were performed as described below. Only difference between the two runs was the amount of KCl added to the solvents, se Table 2:

A solution containing 10.6 mg of rhIL-21 was loaded onto a column (5×105 mm) containing a di-methyl butyl substituted silica gel (15 μm particle diameter, 300 Å pore size). Prior to load the column was equilibrated with 4 CV (column volume) 20 (w/w) % ethanol, 0.21 (w/w) % Tris, X (w/w) % KCl (for X see Table 2), pH 7.0. Unbound protein was washed out with 3 CV 20 (w/w) % ethanol, 0.21 (w/w) % Tris, X (w/w) % KCl (for X see Table 2), pH 7.0. rhIL-21 was eluted with a linear gradient over 25 CV from 20-70 (w/w) % ethanol contained in 0.21 (w/w) % Tris, X (w/w) % KCl (for X see Table 1), pH 7.0. The column was washed with 5 CV 70 (w/w) % ethanol, 0.21 (w/w) % Tris, X (w/w) % KCl (for X see Table 2), pH 7.0 and 5 CV WFI.

The column was regenerated with 5 CV 60 (w/w) % 1-propanol 0.21 (w/w) % Tris, 0.52 (w/w) % KCl, pH 7.0.

The purification was performed at a flow rate of 30 CV/h and at room temperature.

TABLE 2

| Run | Amount KCl in solvents (X) | Yield | Efficiency, N |
| --- | --- | --- | --- |
| 1 | 0 (w/w) % | 74.5% | 1032 |
| 2 | 0.52 (w/w) % | 76.2% | 1299 |

Figure 3:
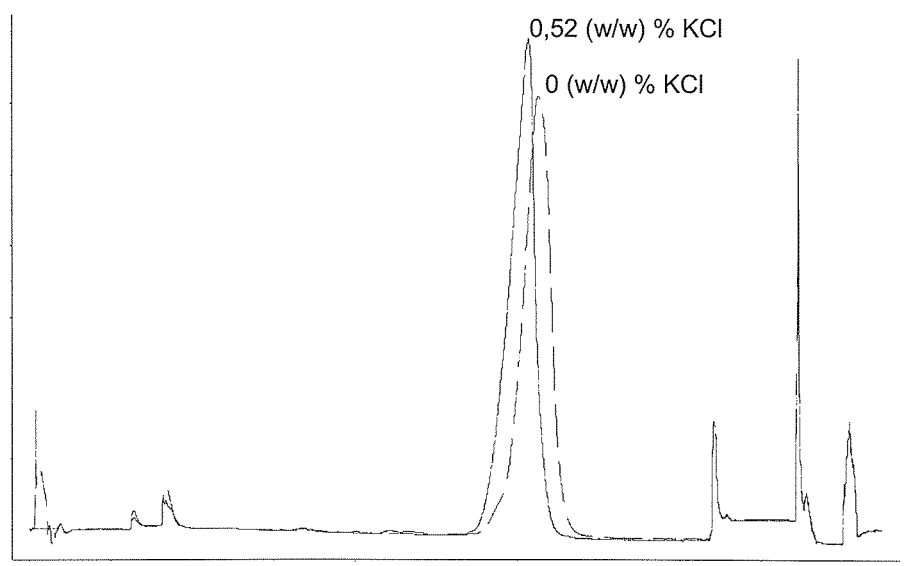
FIG. 3 is an overlay chromatogram from two purifications of IL-21 purified on a di-methyl butyl substituted silica gel with no or 0.52 (w/w) % KCl added as salt to the chromatographic solvents, cf. example 3.

The two chromatograms are shown in FIG. 3. The chromatograms show a KCl dependent difference in retention volume and peak shape of the main peak. The retention volume decreases and the peak becomes narrower when the KCl concentration is raised showing increased efficiency, N (determined by equation 2) when increasing KCl concentration, see Table 2.

Example 4

Performing RPC-Chromatography on a Polystyrene Divenyle Benzene Resin with 0 (w/w) %, 0.52 (w/w) % or 1.12 (w/w) % KCl Respectively Added as Salt to the Chromatographic Solvents Three chromatographic runs were performed as described below. Only difference between the three runs was the amount of KCl added to the solvents, se Table 3:

A solution containing 10.6 mg of rhIL-21 was loaded onto a column (4×125 mm) containing a polystyrene divinyl benzene resin, PLRP-S (Polymer Laboratories, 15 μm particle diameter, 300 Å pore size). Prior to load the column was equilibrated with 4 CV (column volume) 20 (w/w) % ethanol, 0.21 (w/w) % Tris, X (w/w) % KCl (for X see Table 3), pH 7.0. Unbound protein was washed out with 3 CV 20 (w/w) % ethanol, 0.21 (w/w) % Tris, X (w/w) % KCl (for X see Table 3), pH 7.0. rhIL-21 was eluted with a linear gradient over 25 CV from 20-70 (w/w) % ethanol contained in 0.21 (w/w) % Tris, X (w/w) % KCl (for X see Table 1), pH 7.0. The column was washed with 5 CV 70 (w/w) % ethanol, 0.21 (w/w) % Tris, X (w/w) % KCl (for X see Table 3), pH 7.0 and 5 CV WFI.

The column was regenerated with 5 CV 60 (w/w) % 1-propanol 0.21 (w/w) % Tris, 0.52 (w/w) % KCl, pH 7.0.

The purification was performed at a flow rate of 38 CV/h and at room temperature.

TABLE 3

| Run | Amount KCl in solvents (X) | Yield | Efficiency, N |
| --- | --- | --- | --- |
| 1 | 0 (w/w) % | 39.8% | 1815 |
| 2 | 0.52 (w/w) % | 57.3% | 1948 |
| 3 | 1.12 (w/w) % | 72.9% | 2719 |

Figure 4:
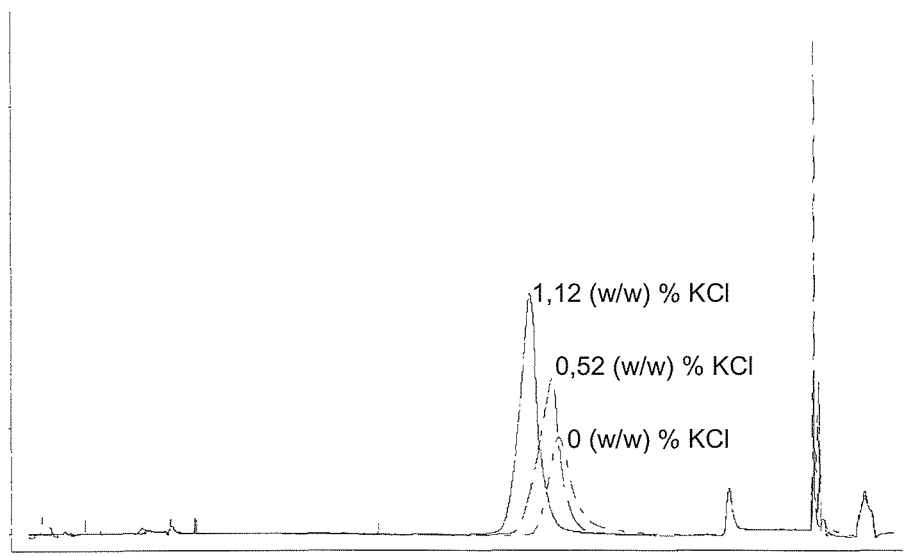
FIG. 4 is an overlay chromatogram from three purifications of IL-21 purified on a polystyrene divinely benzene resin with 0.19 (w/w) %, 0.37 (w/w) % or 0.52 (w/w) % KCl respectively added as salt to the chromatographic solvents, cf. example 4.

The three chromatograms are shown in FIG. 4. The chromatograms show a KCl dependent difference in retention volume and peak shape of the main peak. The retention volume decreases and the peak becomes narrower when the KCl concentration is raised showing increased efficiency (N) when increasing KCl concentration, see Table 3. Yield increases as the concentration of KCl is increased in the solvents.

Example 5

RPC-HPLC purification of rhIL-21 at pH 3.5

A solution containing 20 mg of rhIL-21 was loaded onto a column (5×105 mm) containing a CN-propyl substituted silica gel (15 μm particle diameter, 300 Å pore size). Prior to load the column was equilibrated with 4 CV (column volume) 25 (w/w) % ethanol, 0.23 (w/w) % Na-acetate.$3H_2O$, 0.52 (w/w) % KCl, pH 3.5. Unbound protein was washed out with 3 CV 25 (w/w) % ethanol, 0.23 (w/w) % Na-acetate.$3H_2O$, 0.52 (w/w) % KCl pH 3.5. rhIL-21 was eluted with a linear gradient over 20 CV from 25-70 (w/w) % ethanol contained in 0.23 (w/w) % Na-acetate.$3H_2O$, 0.52 (w/w) % KCl, pH 3.5. The column was washed with 5 CV 70 (w/w) % ethanol, 0.23 (w/w) % Na-acetate.$3H_2O$, 0.52 (w/w) % KCl, pH 3.5 and 5 CV 0.23 (w/w) % Na-acetate.$3H_2O$, 0.52 (w/w) % KCl, pH 3.5. The purification was performed at a flow rate of 30 CV/h and at room temperature.

The column was regenerated with 5 CV 60 (w/w) % 1-propanol 0.21 (w/w) % Tris, 0.52 (w/w) % KCl, pH 7.0.

The IL-21 containing main peak eluted in a relatively broad peak. Based on a small regeneration peak, yield seemed high.

Example 6

RPC-HPLC Purification of rhIL-21 at pH 5.0

A solution containing 20 mg of rhIL-21 was loaded onto a column (5×105 mm) containing a CN-propyl substituted silica gel (15 μm particle diameter, 300 Å pore size). Prior to load the column was equilibrated with 4 CV (column volume) 25 (w/w) % ethanol, 0.23 (w/w) % Na-acetate.$3H_2O$, 0.52 (w/w) % KCl, pH 5.0. Unbound protein was washed out with 3 CV 25 (w/w) % ethanol, 0.23 (w/w) % Na-acetate.$3H_2O$, 0.52 (w/w) % KCl pH 5.0. rhIL-21 was eluted with a linear gradient over 20 CV from 25-70 (w/w) % ethanol contained in 0.23 (w/w) % Na-acetate.$3H_2O$, 0.52 (w/w) % KCl, pH 5.0. The column was washed with 5 CV 70 (w/w) % ethanol, 0.23 (w/w) % Na-acetate.$3H_2O$, 0.52 (w/w) % KCl, pH 5.0 and 5

CV 0.23 (w/w) % Na-acetate.3H$_2$O, 0.52 (w/w) % KCl, pH 5.0. The purification was performed at a flow rate of 30 CV/h and at room temperature.

The column was regenerated with 5 CV 60 (w/w) % 1-propanol 0.21 (w/w) % Tris, 0.52 (w/w) % KCl, pH 7.0.

IL-21 eluted in a relatively sharp main peak and with a with a retention volume relatively higher than at pH 3.5, example 4. Based on a small regeneration peak, yield seemed high.

Example 7

RPC-HPLC Purification of rhIL-21 at pH 9.0

A solution containing 8 mg of rhIL-21 was loaded onto a column (4×125 mm) containing a polystyrene divinyl benzene resin, PLRP-S (Polymer Laboratories, 15 μm particle diameter, 300 Å pore size). Prior to load the column was equilibrated with 4 CV (column volume) 50 (w/w) % ethanol, 0.15 (w/w) % histidine, 0.52 (w/w) % KCl, pH 9.0. Unbound protein was washed out with 3 CV 50 (w/w) % ethanol, 0.15 (w/w) % histidine, 0.26 (w/w) % KCl, pH 9.0. rhIL-21 was eluted with a linear gradient over 15 CV from 50-70 (w/w) % ethanol contained in 0.15 (w/w) % histidine, 0.52 (w/w) % KCl, pH 9.0. The column was washed with 3 CV 70 (w/w) % ethanol, 0.15 (w/w) % histidine, 0.52 (w/w) % KCl, pH 9.0 and 5 CV WFI.

The column was regenerated with 5 CV 60 (w/w) % 1-propanol 0.21 (w/w) % Tris, 0.52 (w/w) % KCl, pH 7.0.

The purification was performed at 30° C. at a flow rate of 19 CV/h.

IL-21 eluted late in the gradient and in a relatively broad peak. Yield was approximately 30%. A relatively large fraction of IL-21 was lost in the regeneration peak.

Example 8

RPC-HPLC Purification of rhIL-21 at pH 7.0 at 30° C., 40° C. or 50° C.

Three chromatographic runs were performed as described below. Only difference between the three runs was the temperature at which the chromatography was performed, see Table 4:

A solution containing 20 mg of rhIL-21 was loaded onto a column (5×102 mm) containing a di-methyl butyl substituted silica gel (15 μm particle diameter, 300 Å pore size). Prior to load the column was equilibrated with 4 CV (column volume) 25 (w/w) % ethanol, 0.21 (w/w) % Tris, 0.52 (w/w) % KCl, pH 7.0. Unbound protein was washed out with 3 CV 25 (w/w) % ethanol, 0.21 (w/w) % Tris, 0.52 (w/w) % KCl pH 7.0. rhIL-21 was eluted with a linear gradient over 20 CV from 25-70 (w/w) % ethanol contained in 0.21 (w/w) % Tris, 0.52 (w/w) % KCl, pH 7.0. The column was washed with 5 CV 70 (w/w) % ethanol, 0.21 (w/w) % Tris, 0.52 (w/w) % KCl, pH 7.0 and 5 CV, 0.21 (w/w) % Tris, 0.52 (w/w) % KCl, pH 7.0.

The column was regenerated with 5 CV 60 (w/w) % 1-propanol 0.21 (w/w) % Tris, 0.52 (w/w) % KCl, pH 7.0. The purifications were performed at a flow rate of 30 CV/h and at temperature as shown in Table 4.

Figure 5:
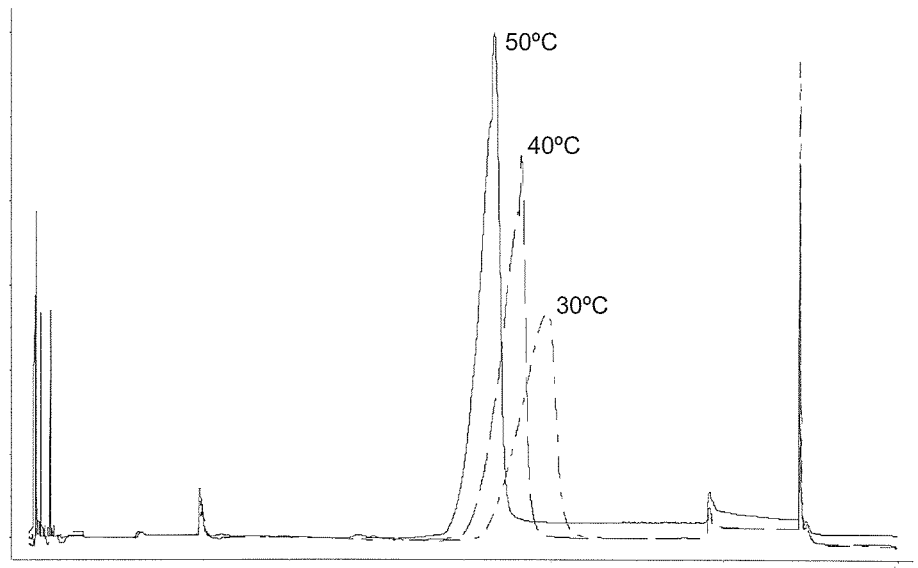
FIG. 5 is an overlay chromatogram from three purifications of IL-21 purified on a di-methyl butyl substituted silica gel at 30° C., 40° C. and 50° C. respectively, cf. example 8.

An overlay chromatogram of the three purifications is shown in FIG. 5. The chromatogram shows, that the main peak narrows and that retention volume decreases when temperature is raised from 30-50° C.

TABLE 4

| Run | Temperature |
|---|---|
| 1 | 30° C. |
| 2 | 40° C. |
| 3 | 50° C. |

Example 9

RPC-HPLC Purification of rhIL-21 using NaCl as Salt in the Chromatographic Solvents A solution containing 10.6 mg of rhIL-21 was loaded onto a column (5×108 mm) containing a CN-propyl substituted silica gel (15 μm particle diameter, 300 Å pore size). Prior to load the column was equilibrated with 4 CV (column volume) 20 (w/w) % ethanol, 0.21 (w/w) % Tris, 0.41 (w/w) % NaCl, pH 7.0. Unbound protein was washed out with 3 CV 20 (w/w) % ethanol, 0.21 (w/w) % Tris, 0.41 (w/w) % NaCl, pH 7.0. rhIL-21 was eluted with a linear gradient over 20 CV from 20-80 (w/w) % ethanol contained in 0.21 (w/w) % Tris, 0.41 (w/w) % NaCl, pH 7.0. The column was washed with 5 CV 80 (w/w) % ethanol, 0.21 (w/w) % Tris, pH 7.0, 0.41 (w/w) % NaCl and 5 CV water for injection (WFI).

The column was regenerated with 3 CV 60 (w/w) % 1-propanol 0.21 (w/w) % Tris, 0.52 (w/w) % KCl, pH 7.0.

The purification was performed at a flow rate of 30 CV/h and at 30° C.

IL-21 eluted in a well defined tall peak approximately in the middle of the gradient. Pool volume was approximately 2 column volume.

Example 10

RPC-HPLC Purification of rhIL-21 Using NH$_4$Cl as Salt in the Chromatographic Solvents A solution containing 10.6 mg of rhIL-21 was loaded onto a column (5×108 mm) containing a CN-propyl substituted silica gel (15 μm particle diameter, 300 Å pore size). Prior to load the column was equilibrated with 4 CV (column volume) 20 (w/w) % ethanol, 0.21 (w/w) % Tris, 0.37 (w/w) % NH$_4$Cl, pH 7.0. Unbound protein was washed out with 3 CV 20 (w/w) % ethanol, 0.21 (w/w) % Tris, 0.37 (w/w) % NH$_4$Cl, pH 7.0. rhIL-21 was eluted with a linear gradient over 20 CV from 20-80 (w/w) % ethanol contained in 0.21 (w/w) % Tris, 0.37 (w/w) % NH$_4$Cl, pH 7.0. The column was washed with 5 CV 80 (w/w) % ethanol, 0.21 (w/w) % Tris, 0.37 (w/w) % NH$_4$Cl, pH 7.0 and 5 CV water for injection (WFI).

The column was regenerated with 3 CV 60 (w/w) % 1-propanol 0.21 (w/w) % Tris, 0.52 (w/w) % KCl, pH 7.0.

The purification was performed at a flow rate of 30 CV/h and at 30° C.

IL-21 eluted in a well defined tall peak approximately in the middle of the gradient. Pool volume was approximately 2 column volume.

Example 11

RPC-HPLC Purification of rhIL-21 Using Potassium Lactate as Salt in the Chromatographic Solvents A solution containing 10.6 mg of rhIL-21 was loaded onto a column (5×105 mm) containing a di-methyl butyl substituted silica gel (15 μm particle diameter, 300 Å pore size). Prior to load the column was equilibrated with 4 CV (column volume) 20 (w/w) % ethanol, 0.21 (w/w) % Tris, 0.32 (w/w) % potassium lactate, pH 7.0. Unbound protein was washed out with 3 CV 20 (w/w) % ethanol, 0.21 (w/w) % Tris, 0.32 (w/w) % potassium lactate, pH 7.0. rhIL-21 was eluted with a linear gradient over 20 CV from 20-70 (w/w) % ethanol contained in 0.21 (w/w) % Tris, 0.32 (w/w) % potassium lactate, pH 7.0. The column was washed with 5 CV 70 (w/w) % ethanol, 0.21 (w/w) % Tris, 0.32 (w/w) % potassium lactate, pH 7.0 and 5 CV water for injection (WFI).

The column was regenerated with 3 CV 60 (w/w) % 1-propanol 0.21 (w/w) % Tris, 0.52 (w/w) % KCl, pH 7.0.

The purification was performed at a flow rate of 30 CV/h and at 30° C.

IL-21 eluted in a sharp main peak and in a volume of approximately 2 column volumes. The protein eluted relatively late in the gradient. Yield was approximately 75%. Approximately 20% IL-21 was lost in the regeneration peak.

Example 12

Performing RP-HPLC on an Octadecyl Substituted Silica Resin

A solution containing 31.8 mg of rhIL-21 was loaded onto a column (4×250 mm) containing a octadecyl substituted silica gel (15 µm particle diameter, 300 Å pore size). Prior to load the column was equilibrated with 4 CV (column volume) 40 (w/w) % ethanol, 0.21 (w/w) % Tris, 0.52 (w/w) % KCl, pH 7.0. Unbound protein was washed out with 1 CV 40 (w/w) % ethanol, 0.21 (w/w) % Tris, 0.52 (w/w) % KCl, pH 7.0. rhIL-21 was eluted with a linear gradient over 20 CV from 40-70 (w/w) % ethanol contained in 0.21 (w/w) % Tris, 0.52 (w/w) % KCl, pH 7.0. The column was washed with 3 CV 70 (w/w) % ethanol, 0.21 (w/w) % Tris, 0.52 (w/w) % KCl, pH 7.0.

The purification was performed at room temperature at a flow rate of 6 CV/h.

IL-21 eluted in a relatively broad peak due to tailing on the trailing edge. Yield was approximately 50%

Example 13

Purifying Human Growth Hormone (hGH) Using RPC with No Salt Added to Solvents

Solvent A was 0.61 (w/w) % Tris, pH 7.5. Solvent B was 40 (w/w) % 1-propanol, 0.61 (w/w) % Tris, pH 7.5. 3 mg of freeze dried hGH was dissolved in 3 ml of solvent A. The solution was loaded onto a column (4×125 mm) containing a polystyrene divenyle benzene resin, PLRP-S (Polymer Laboratories, 15 µm particle diameter, 300 Å pore size). Prior to load the column was equilibrated with 5 CV 30% solvent A+70% solvent B. Unbound impurities were washed out with 3 CV of 30% solvent A+70% solvent B.

hGH was eluted with a linear gradient over 10 CV from 30% solvent A+70% solvent B to 100% solvent B. The column was regenerated with 5 CV solvent B. The purification was performed at room temperature at a flow rate of 7.5 CV/h. HGh eluted in a well defined peak (solid line in FIG. 6). The protein eluted approximately in the middle of the gradient.

Example 14

Purifying Human Growth Hormone (hGH) Using RPC with KCl Added to Solvents

Solvent A was 0.61 (w/w) % Tris, 0.75% KCl, pH 7.5. Solvent B was 40 (w/w) % 1-propanol, 0.75% KCl, 0.61 (w/w) % Tris, pH 7.5.

3 mg of freeze dried hGH was dissolved in 3 ml of 0.61 (w/w) % Tris, pH 7.5. The solution was loaded onto a column (4×125 mm) containing a polystyrene divinyl benzene resin, PLRP-S (Polymer Laboratories, 15 µm particle diameter, 300 Å pore size). Prior to load the column was equilibrated with 5 CV 30% solvent A+70% solvent B. Unbound impurities were washed out with 3 CV of 30% solvent A+70% solvent B.

HGH was eluted with a linear gradient over 10 CV from 30% solvent A+70% solvent B to 100% solvent B. The column was regenerated with 5 CV solvent B. The purification was performed at room temperature at a flow rate of 7.5 CV/h.

IL-21 eluted in well defined peak in the beginning of the gradient. Compared to example 13 the peak was narrower and taller indicating better chromatographic performance than in example 13. Only difference between this run and the run in example 13 was the addition of KCl to the solvents in this example, indicating that KCl is responsible for the increased performance.

Example 15

Purifying Human Growth Hormone (hGH) Using RPC with KCl Added to Solvents

This chromatographic run was performed in order to investigate whether the taller and more narrow peak in example 14 compared to example 13 was due to the fact that the main peak eluted with a smaller retention volume in example 14. This was done by adjusting the gradient from example 14 so that the hGH main peak eluted at approximately the same retention volume as in example 13.

As in example 14 solvent A was 0.61 (w/w) % Tris, 0.75% KCl, pH 7.5. Solvent B was 40 (w/w) % 1-propanol, 0.75% KCl, 0.61 (w/w) % Tris, pH 7.5.

3 mg of freeze dried hGH was dissolved in 3 ml of 0.61 (w/w) % Tris, pH 7.5. The solution was loaded a onto a column (4×125 mm) containing a polystyrene divinyle benzene resin, PLRP-S (Polymer Laboratories, 15 µm particle diameter, 300 Å pore size). Prior to load the column was equilibrated with 5 CV 35.3% solvent A+64.7% solvent B. Unbound impurities were washed out with 3 CV of 35.3% solvent A+64.7% solvent B.

HGh was eluted with a linear gradient over 10 CV from 35.3% solvent A+64.7% solvent B to 5.3% solvent A+94.7% solvent B. The column was regenerated with 5 CV solvent B. The purification was performed at room temperature at a flow rate of 7.5 CV/h.

Figure 6:
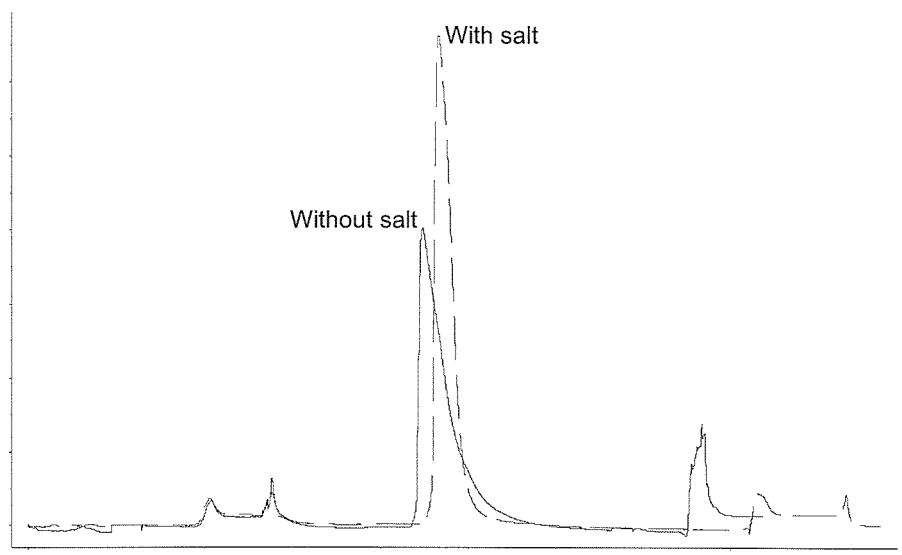
FIG. 6 is an overlay of the chromatograms obtained in example 13 (solid line) and 15 (dashed line), showing that the addition of salt to the chromatographic solvents makes the main peak narrower and taller and thus increases the chromatographic performance.

The IL-21 peak (dashed line in FIG. 6) eluted in a well defined peak, approximately in the middle of the gradient with a retention volume comparable to the retention volume of the main peak in example 13, see FIG. 6. The peak was taller and narrower than in example 13 (where no salt was added to the solvents), showing that the increase in chromatographic performance was because of the addition of salt and not due to the lower retention volume.

The invention claimed is:
1. A method for purifying interleukin 21 (IL-21) from one or more samples, wherein each sample comprises and at least one undesired impurity, the method for each sample comprising:
　(a) loading dissolved IL-21 onto a RPC-column, equilibrated with a solvent comprising water, 25-35 (w/w) % ethanol, 0.1-0.3 (w/w) % Tris, 0.5-1.0 (w/w) % KCl, pH 6-8, up to 20 g/l column material;
　(b) washing the column with up to 5 column volumes of the equilibrating solvent;

(c) eluting IL-21 in a linear gradient of 0 to 100% of a eluting solvent comprising 50-70% (w/w) % ethanol, 0.1-0.3 (w/w) % Tris, 0.5-1.0 (w/w) % KCl, pH 6-8;
(d) collecting the IL-21 containing fractions;
(e) washing the column with up to 10 column volumes of the eluting solvent; and
(f) regenerating the column with a 50-70% 1-propanol containing solution.

2. The method of claim 1, wherein the chromatographic temperature is in the range of 0-80° C.

3. The method of claim 1, wherein said method is performed using a silica based chromatographic resin.

4. The method of claim 3, wherein said resin is substituted with a hydrophobic ligand that is an aliphate derivative.

5. The method of claim 1, wherein said method is performed using a polystyrene based chromatographic resin.

6. The method of claim 1, wherein said at least one undesired impurity is selected from a group consisting of host cell proteins, truncated forms, extended forms, deamidated forms, incorrectly folded forms, forms with undesired glycosylation, oxidated forms, forms resulting from racemization, forms lacking amino acids in the intra-polypeptide chain, forms having extra amino acids in the intra-polypeptide chain, forms having replacements of amino acids in the intra-polypeptide chain, forms wherein a chemical or enzymatic modification has taken place on another residue than desired, non-protein impurities, and a mixture thereof 7. The method of claim 1, wherein the said IL-21 is loaded onto the column in a concentration of 0.1-200 mg per mL of resin.

8. The method of claim 7, wherein said process is an industrial-scale process.

9. The method of claim 7, wherein the said IL-21 is loaded onto the column in a concentration of at least 0.1 mg per mL of resin.

* * * * *

UNITED STATES PATENT AND TRADEMARK OFFICE
CERTIFICATE OF CORRECTION

| | | |
|---|---|---|
| PATENT NO. | : 8,921,518 B2 | Page 1 of 1 |
| APPLICATION NO. | : 12/158759 | |
| DATED | : December 30, 2014 | |
| INVENTOR(S) | : Daniel E. Rasmussen et al. | |

It is certified that error appears in the above-identified patent and that said Letters Patent is hereby corrected as shown below:

In the Claims

At column 18, claim number 6, line number 9, please insert a --.-- after "...thereof".

Signed and Sealed this
Twenty-third Day of February, 2016

Michelle K. Lee
*Director of the United States Patent and Trademark Office*